US012807563B2

(12) United States Patent
Chen et al.

(10) Patent No.: US 12,807,563 B2
(45) Date of Patent: Nov. 24, 2026

(54) PREPARATION METHOD FOR SARCOSINE AND DERIVATIVES THEREOF

(71) Applicant: QIANJIANG YONGAN PHARMACEUTICAL CO., LTD., Qianjiang (CN)

(72) Inventors: Yong Chen, Qianjiang (CN); Xiquan Fang, Qianjiang (CN); Shaobo Li, Qianjiang (CN); Wei Zhou, Qianjiang (CN); Feng Liu, Qianjiang (CN); Xiang Li, Qianjiang (CN); Weihao Wu, Qianjiang (CN); Wei Zhou, Qianjiang (CN); Mingjiao Zhao, Qianjiang (CN); Na Luo, Qianjiang (CN)

(73) Assignee: QIANJIANG YONGAN PHARMACEUTICAL CO., LTD., Qianjiang (CN)

( * ) Notice: Subject to any disclaimer, the term of this patent is extended or adjusted under 35 U.S.C. 154(b) by 579 days.

(21) Appl. No.: 18/244,919

(22) Filed: Sep. 12, 2023

(65) Prior Publication Data

US 2024/0351976 A1 Oct. 24, 2024

(30) Foreign Application Priority Data

Apr. 23, 2023 (CN) ........................ 202310439872.7

(51) Int. Cl.

| | |
|---|---|
| ***C07C 231/02*** | (2006.01) |
| ***C07C 227/00*** | (2006.01) |
| ***C07C 227/04*** | (2006.01) |
| ***C07C 249/02*** | (2006.01) |

(52) U.S. Cl.

CPC .......... *C07C 231/02* (2013.01); *C07C 227/00* (2013.01); *C07C 227/04* (2013.01); *C07C 249/02* (2013.01)

(58) Field of Classification Search

CPC .... C07C 231/02; C07C 227/04; C07C 249/02
See application file for complete search history.

(56) References Cited

U.S. PATENT DOCUMENTS

| | | | | |
|---|---|---|---|---|
| 5,719,319 | A * | 2/1998 | Weiss | C07C 277/02 562/560 |
| 6,180,759 | B1 * | 1/2001 | Mencel | C07D 211/34 562/443 |
| 2009/0163739 | A1 * | 6/2009 | Thalhammer | C07C 277/08 562/560 |
| 2019/0008813 | A1 * | 1/2019 | Tsai | A61K 31/5513 |

OTHER PUBLICATIONS

Elokdah, H. et al., Desig, synthesis and Biological Evaluation of Thio-containing Compounds with Serum HDL-cholesterol-elevatig properties, Jornal of Med. Chem., vol. 47, issue 3, pp. 618-695 (Year: 2004).*

Yu, et al., Glycine crystallization during spray drying: the pH effect on salt and polymorphic forms, Journal of Pharmaceutical sciences, vol. 91, No. 11, pp. 2367-2375 (Year: 2002).*

* cited by examiner

*Primary Examiner* — Yate' K Cutliff

(74) *Attorney, Agent, or Firm* — Kilpatrick Townsend & Stockton LLP

(57) ABSTRACT

The present invention relates to a preparation method for a sarcosinate including: step 1, reacting a solution of glyoxylic acid or a glyoxylate with an amine solution to prepare a Schiff base solution; step 2, subjecting the prepared Schiff base solution to a hydrogenation reaction under the condition of a catalyst; and step 3, adjusting a pH value of a solution obtained after the hydrogenation reaction to be alkaline to obtain the sarcosinate. Wherein the pH value of the solution obtained after the hydrogenation reaction in the step 3 is adjusted to be acidic to obtain sarcosine. Wherein a sarcosinate solution obtained in the step 3 is reacted with cyanamide to prepare a sarcosine derivative. A novel preparation method for sarcosine and derivatives thereof in the present invention solves the problem of using highly toxic chemicals as raw materials in the existing production process of sarcosine or sarcosine derivatives such as creatine, while the new process is simpler and more efficient, has lower production cost, and is of great significance.

20 Claims, No Drawings

PREPARATION METHOD FOR SARCOSINE AND DERIVATIVES THEREOF

CROSS-REFERENCE TO RELATED APPLICATION

This application claims the benefit of and the priority to Chinese Patent Application No. 202310439872.7, filed Apr. 23, 2023, entitled "NOVEL PREPARATION METHOD FOR SARCOSINE AND DERIVATIVES THEREOF," the disclosure of which is incorporated by reference herein in its entirety for all purposes.

TECHNICAL FIELD

The present invention relates to techniques for the preparation of sarcosine and derivatives thereof, and in particular to a novel preparation method for sarcosine and derivatives thereof.

BACKGROUND

Sodium sarcosinate, also known as sodium N-methylglycinate, is an amino acid surfactant that appears as a colorless to pale yellow liquid. Sodium sarcosinate is extremely soluble in water, slightly soluble in ethanol, alkaline in aqueous solution, easily decomposed by heating, and partially decomposed into dimethylamine and carbon dioxide. Sodium sarcosinate has the characteristics of no irritation, easy biodegradation, sterilization, and the like, and is widely used in the fields of daily chemical products, health care products, dyes, pharmaceuticals, chemical industry and the like. In the field of daily chemical products, sodium sarcosinate can be used as an active agent to make advanced medicinal soaps, shampoos, toothpastes and other products; in the field of health care products, sodium sarcosinate can be used for preparing creatine, and creatine is a nutritional preparation with the effects of promoting cell growth, providing energy and the like: in the field of dyes, sodium sarcosinate can be used as a dyeing aid; and in the field of chemical industry, sodium sarcosinate can be used to prepare creatine monohydrate, creatine, N-acylsarcosine and sodium salts.

Creatine is a derivative of sarcosine, a white powder crystal, odorless, and slightly bitter, has a molecular formula of C4H9N3O2, and a molecular weight of 131.13, and is soluble in water, slightly soluble in cold water, and insoluble in anhydrous ethanol, diethyl ether and acetone. Creatine is a natural nutrient that exists in the human body, and the creatine in the human body is synthesized in the liver, kidney and pancreas. Creatine plays an important role in promoting the synthesis of nucleic acids and proteins, increasing the reserve of energy substances in the body, promoting the growth of muscles, as well as delaying fatigue and accelerating the physical recovery.

There are three main methods for the preparation of sodium sarcosinate, one of which is a chloroacetic acid method, namely chloroacetic acid is reacted with monomethylamine under the action of sodium hydroxide; the chloroacetic acid method needs to be carried out under pressurized conditions, the reaction condition is relatively high, the requirement for equipment used in large-scale industrial production is high, and the yield is not high, only about 50%. Wherein a large amount of methylamine hydrochloride is generated in the reaction, which brings difficulties to the subsequent product purification; moreover, a product produced by this method has a bitter taste and needs to be treated by a debittering agent such as sodium thiosulfate and the like, and the post-treatment process is complicated. Meanwhile, the preparation process is accompanied by the production of highly corrosive hydrogen chloride gas, and the hydrogen chloride gas is easily dissolved in water to form hydrochloric acid with strong corrosivity, so that reaction equipment and a gas recovery device must adopt materials with acid corrosion resistance, the investment cost is high, and the equipment maintenance cost is high.

U.S. Pat. No. 3,479,388A and Chinese patent CN103664665A respectively introduced the preparation of sodium sarcosinate by a hydroxyacetonitrile method. The hydroxyacetonitrile method can also be called a hydrocyanic acid method, i.e., hydrocyanic acid and formaldehyde directly participate in the reaction. A main process is that hydroxyacetonitrile reacts with monomethylamine, followed by alkaline hydrolysis with liquid caustic soda to generate sodium sarcosinate. The hydroxyacetonitrile method is currently a relatively common method for the production of sodium sarcosinate in China, but this method still has the problems of low yield and the like in practical application. At the same time, hydrocyanic acid and derivatives thereof are highly toxic and belong to a regulatory category of highly toxic chemicals, have difficulties in transportation, production and wastewater treatment, and also cause problems such as high management costs and environmental risks during transportation and use, which make it difficult to control product quality.

In addition. Chinese patent CN101003488A proposes a method for the preparation of sodium sarcosinate by using methylmonoethanolamine. The method has a single raw material supply, and in addition, the process needs high temperature and high pressure, has high energy consumption cost, and is not conducive to industrial production.

At present, the hydroxyacetonitrile method is mainly adopted for the industrial production of sodium sarcosinate, and this method faces the problems of using highly toxic raw materials, many by-products, low yield, unstable product quality and high production operation control difficulty and the like. Therefore, it is urgent to solve the problems of low product quality, high production cost, much pollution caused by "three wastes" and the use of highly toxic chemicals in the existing production of sodium sarcosinate and derivatives thereof, and a new method for synthesizing sodium sarcosinate and derivatives thereof needs to be developed.

SUMMARY

A purpose of the present invention is to provide a preparation method for a sarcosinate, which is used for solving the problems that highly toxic chemicals are used as raw materials in the existing production process of sarcosine or sarcosine derivatives such as creatine and the like, the process is complicated, and the production cost is high.

The present invention relates to a preparation method for a sarcosinate, including: step 1, reacting a solution of glyoxylic acid or a glyoxylate with an amine solution to prepare a Schiff base solution; step 2, subjecting the prepared Schiff base solution to a hydrogenation reaction under the condition of a catalyst; and step 3, adjusting a pH value of a solution obtained after the hydrogenation reaction to be alkaline to obtain the sarcosinate.

According to one example of the preparation method the present invention, a general formula for a chemical structure of glyoxylic acid is:

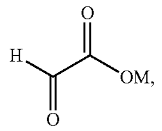

wherein M is $H^+$:

a general formula for a chemical structure of the glyoxylate is:

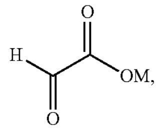

wherein M is $NH_4^+$, $RNH_3^+$, $Li^+$, $Na^+$, $K^+$, $Ca^{2+}$ or $Mg^{2+}$; and a general formula for a chemical structure of a Schiff base is:

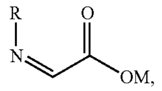

wherein the R group is —H, -Me, -Et, C1-C20 alkyl, C1-C20 alkenyl, C3-C8 cycloalkyl or C6-C20 aryl, and preferably, the R group is —H or -Me.

According to one example of the preparation method the present invention, in the step 2, the hydrogenation reaction adopts an intermittent catalytic hydrogenation reaction, a fixed-bed continuous catalytic hydrogenation reaction or a fixed-bed semi-continuous catalytic hydrogenation reaction; and a solvent for the hydrogenation reaction is $H_2O$/R'OH, wherein R' is C1-C6 alkyl; wherein the intermittent hydrogenation reaction is carried out for 1-24 hours, preferably 8-16 hours; wherein the amount of a catalyst used in for the intermittent hydrogenation reaction is 0.01 wt %-2 wt %; wherein a weight hourly space velocity of the fixed-bed continuous catalytic hydrogenation is 0.1 $h^{-1}$-1.0 $h^{-1}$, preferably 0.2 $h^{-1}$-0.5 $h^{-1}$.

According to one example of the preparation method the present invention, in the step 1, the amount of an amine used in the amine solution is 1-6 equivalents; the amine solution is an aqueous or alcoholic solution of the amine, the aqueous or alcoholic solution of the amine having a mass percent concentration of 10% to 60%, preferably 30% to 40%; and a general formula for a chemical structure of the amine is $RNH_2$, wherein the R group is —H, -Me, -Et, C1-C20 alkyl, C1-C20 alkenyl, C3-C8 cycloalkyl or C6-C20 aryl, preferably ammonia, methylamine or aromatic amine.

According to one example of the preparation method the present invention, the solution of glyoxylic acid or glyoxylate is reacted with the amine solution is at a temperature of −10° C., to 40° C.

According to one example of the preparation method the present invention, in the step 2, a solvent system for the hydrogenation reaction is an alcohol plus water system or a water system; wherein a volume ratio of the water to the alcohol is 1:0-1:10, and preferably, the volume ratio of the water to the alcohol is 1:0-1:2.

According to one example of the preparation method the present invention, in the step 2, the catalyst is one or more of Pd, Ni, Pt, Ru, Rh, $NaBH_4$, $NaCNBH_3$, $LiBH_4$, diisobutyl aluminium hydride, iron powder and zinc powder, preferably a Pd or Ni metal catalyst; wherein a carrier of the catalyst is alumina, zeolite, activated carbon, SiO2, ceramic balls, sea sand, graphite, inorganic glass, organic glass, optical fiber, glass fiber, natural clay, foamed plastic, resin, wood chips or expanded perlite, preferably activated carbon, alumina, zeolite or SiO2.

According to one example of the preparation method the present invention, in the step 2, the hydrogenation reaction is carried out under a pressure of 0.1-10 MPa, preferably 2-5 MPa; and the hydrogenation reaction is carried out at a temperature of 20-150° C., preferably 30-100° C.

According to one example of the preparation method the present invention, in the step 3, the pH value of the solution is adjusted to a desired alkaline value after the solution is treated by an acid, an alkali, electrodialysis or ion exchange resin depending on the pH value of the solution.

According to one example of the preparation method the present invention, in the step 3, the acid is an inorganic acid or an organic acid, preferably sulfuric acid, hydrochloric acid, phosphoric acid, formic acid or acetic acid; the alkali is an inorganic metal hydroxide, inorganic ammonia or an organic amine, preferably lithium hydroxide, sodium hydroxide, potassium hydroxide, ammonia or methylamine; and the ion exchange resin is acidic ion exchange resin or alkaline ion exchange resin.

The present invention also provides a preparation method for a sarcosine derivative, wherein a sarcosinate solution is prepared by using the preparation method described above, and the method further include: step 4, reacting the sarcosinate solution with cyanamide to prepare the sarcosine derivative.

According to one example of the preparation method the present invention, the sarcosine derivative is creatine, creatine monohydrate or a creatine salt.

According to one example of the preparation method the present invention, after the sarcosinate solution is reacted with cyanamide, crystallization separation is performed to prepare creatine monohydrate.

According to one example of the preparation method the present invention, after the sarcosinate solution is reacted with cyanamide, crystallization separation and drying dehydration are performed to prepare creatine.

According to one example of the preparation method the present invention, the pH value of the solution obtained after the hydrogenation reaction is adjusted to be greater than 7 and less than or equal to 11.

According to one example of the preparation method the present invention, after cyanamide is added into the sarcosinate solution for a reaction, an alkali is added, and a pH value is adjusted to be greater than 7 to obtain the creatine salt.

According to one example of the preparation method the present invention, after cyanamide is added into the sarcosinate solution for a reaction, an alkali is added, and a pH value is adjusted to be greater than 7 to obtain a salt sarcosine derivative.

The present invention also provides a preparation method for sarcosine, wherein the pH value of the solution obtained after the hydrogenation reaction in the step 3 of the preparation method described above is adjusted to be acidic to obtain the sarcosine.

According to one example of the preparation method the present invention, in the step 3, the pH value of the solution is adjusted to be acidic after the reaction solution obtained after hydrogenation is treated by an acid, electrodialysis or acidic ion exchange resin.

According to one example of the preparation method the present invention, in the step 3, the acid is an inorganic acid or an organic acid, preferably sulfuric acid, hydrochloric acid, phosphoric acid, formic acid or acetic acid.

The present invention provides a novel preparation method for sarcosine and derivatives thereof, which solves the problem of using highly toxic chemicals as raw materials in the existing production process of sarcosine or sarcosine derivatives such as creatine, while the new process is simpler and more efficient, has lower production cost, and is of great significance.

DETAILED DESCRIPTION

In order to make the objects, contents, and advantages of the present invention more apparent, specific embodiments of the present invention are described in further detail below with reference to the Examples.

The present invention is further illustrated below by way of Examples, but the present invention is not thereby limited to the scope of the described Examples.

Aiming at the problems that in the existing production process of sarcosine derivatives of glycine, sarcosine, creatine and the like having a chemical general structural formula similar to that of such substances, highly toxic raw materials such as hydroxyacetonitrile and the like are needed, as well as the raw materials in the preparation method are expensive, and the reaction condition requirements are high, and the like, the inventors of the present invention have obtained a novel preparation method for sarcosine and derivatives thereof through a long period of test and development. The preparation method of the present invention can be applied to the preparation of various sarcosine and derivatives thereof with similar chemical general structural formulas in practice, instead of being limited to specific sarcosine and derivatives thereof in the following Examples.

Example 1 of the present invention provides a preparation method for a sarcosinate, including:

- step 1, reacting glyoxylic acid or a glyoxylate with an amine to prepare a Schiff base solution;
- step 2, subjecting the resulting Schiff base solution to a hydrogenation reaction under the condition of a catalyst; and
- step 3, adjusting a pH value of a solution obtained after the hydrogenation reaction in the step 2 to be alkaline to obtain the sarcosinate.

Wherein a chemical reaction for the preparation of the sarcosinate takes a sodium salt as an example, specifically:

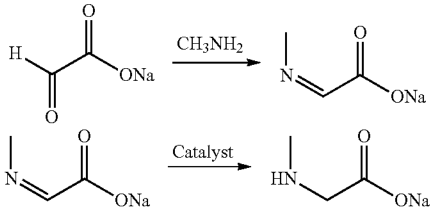

- wherein the mass percentage concentration of glyoxylic acid in the step 1 may be 10%-50%;
- wherein the glyoxylate in the step 1 was prepared by a neutralization reaction of glyoxylic acid with an alkali, wherein the used alkali was an inorganic metal hydroxide, inorganic ammonia, an organic amine, or the like, preferably lithium hydroxide, sodium hydroxide, potassium hydroxide, ammonia, or methylamine.

Wherein a general formula for a chemical structure of the amine in the step 1 is $RNH_2$. Wherein the R group is —H, -Me, -Et, C1-C20 alkyl, C1-C20 alkenyl, C3-C8 cycloalkyl or C6-C20 aryl, and the amine was preferably ammonia, methylamine or arylamine.

Wherein the amount of the amine used in the step 1 was controlled to be 1 to 6 equivalents, preferably 1.0 to 2.0 equivalents:

- wherein the reaction temperature in the step 1 was controlled at −10° C., to 40° C.

Wherein methanol or ethanol can be added into the reaction solution in the step 2, wherein a volume ratio of water to alcohol was preferably 1:0-1:2; and wherein the catalyst for the hydrogenation reaction in the step 2 was mainly Pd, Ni, Pt, Ru, Rh, $NaBH_4$, $NaCNBH_3$, $LiBH_4$, diisobutyl aluminum hydride, iron powder, zinc powder, or the like, preferably a Pd or Ni metal catalyst. Wherein the catalyst can be loaded onto carriers such as alumina, zeolite, activated carbon, SiO2, ceramic balls, sea sand, graphite, inorganic glass, organic glass, optical fiber, glass fiber, natural clay, foamed plastic, resin, wood chips, expanded perlite and the like.

Wherein the amount of the metal catalyst used in the step 2 was 0.01 wt % to 2 wt %, and the reaction was carried out for 1-24 h.

Wherein the hydrogenation reaction in the step 2 was carried out under a pressure of 0.1-10 MPa at a temperature of 20-150° C., and

- wherein the reaction in the step 2 may be a batch reaction or a continuous reaction, preferably the continuous reaction. If the continuous reaction was adopted in the step 2, a weight hourly space velocity of a reaction material was 0.1 $h^{-1}$-1.0 $h^{-1}$, preferably 0.2 $h^{-1}$-0.5 $h^{-1}$.

Wherein a treatment method in the step 3 in this example was determined by a pH of a material obtained by the reaction in the step 2. When the pH of the obtained material was acidic, an alkali (such as an inorganic metal hydroxide, inorganic ammonia, an organic amine, alkaline resin or the like) can be used to adjust the pH to be alkaline to obtain the sarcosinate. Wherein the alkali was preferably lithium hydroxide, sodium hydroxide, potassium hydroxide, ammonia, methylamine or alkaline resin.

Example 2 of the present invention provides a preparation method for sarcosine, including:

- step 1, reacting glyoxylic acid or a glyoxylate with an amine to prepare a Schiff base solution;
- step 2, subjecting the resulting Schiff base solution to a hydrogenation reaction under the condition of a catalyst; and
- step 3, adjusting a pH value of a solution obtained by the reaction in the step 2 to be less than 7 to obtain the sarcosine;

Wherein a chemical reaction for preparing the sarcosine takes a sodium salt as an example, specifically:

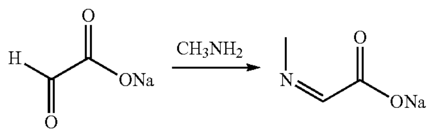

-continued

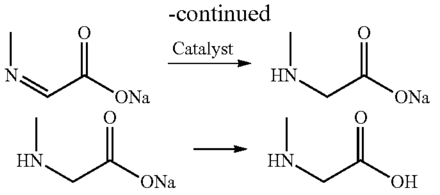

In this example, when a pH of a material obtained by the reaction in the step 2 was alkaline, an acid (such as an inorganic acid, an organic acid, acidic resin, electrodialysis or the like) can be used to adjust the pH to be acidic to obtain the sarcosine, wherein sulfuric acid, hydrochloric acid, phosphoric acid, formic acid, acetic acid or acidic ion exchange resin was preferred.

Example 3 of the present invention provides a preparation method for creatine monohydrate, including:

step 1, reacting glyoxylic acid or a glyoxylate with an amine to prepare a Schiff base solution;

step 2, subjecting the resulting Schiff base solution to a hydrogenation reaction under the condition of a catalyst;

step 3, adjusting a pH value of a material obtained by the reaction in the step 2 to be between 7 or more and 11; and step 4, reacting a material obtained in the step 3 with cyanamide to produce creatine, and then performing crystallization separation to obtain creatine monohydrate.

Wherein creatine monohydrate has the same main structure as creatine, a difference was that a final product creatine monohydrate contained water of crystallization and creatine did not contain water of crystallization, so a chemical structure of creatine monohydrate can refer to that of creatine.

The step 1 and the step 2 of this example were the same as those of the preparation method for the sarcosinate. In the step 3, different adjustments were made according to the pH of the material obtained by the reaction in the step 2, an acidic compound (such as an inorganic acid, an organic acid, acidic resin, electrodialysis or the like) or an alkaline compound (such as an inorganic metal hydroxide, inorganic ammonia, an organic amine, alkaline resin, or the like) may be used to adjust the pH to be greater than 7 to less than or equal to 11. Wherein the acid was preferably sulfuric acid, hydrochloric acid, phosphoric acid, formic acid, acetic acid or acidic resin; wherein the alkali was preferably lithium hydroxide, sodium hydroxide, potassium hydroxide, ammonia, methylamine or alkaline resin; wherein the pH value was preferably 9-10.

In the step 4, a solution of sarcosine/sarcosinate of which a pH value was adjusted to an alkaline range reacted with an aqueous cyanamide solution for a certain time while keeping the temperature; after the reaction was finished, the temperature was slowly lowered under stirring, crystallization was performed while keeping the temperature, and solid-liquid separation was performed to obtain a crude product of creatine monohydrate, and the crude product of creatine monohydrate was refined by purified water and dried to obtain a high-purity finished product of creatine monohydrate. Wherein a mother liquor obtained by centrifugation can be returned to the previous steps 1-4, and elements needed in the mother liquor, such as water and alcohol, can be utilized to recycle the mother liquor.

Example 4 of the present invention provides a method for the preparation of anhydrous creatine, including:

step 1, reacting glyoxylic acid or a glyoxylate with an amine to prepare a Schiff base solution;

step 2, subjecting the resulting Schiff base solution to a hydrogenation reaction under the condition of a catalyst;

step 3, adjusting a pH value of a material obtained by the reaction in the step 2 to be between greater than 7 and less than or equal to 11; and step 4, reacting a material obtained in the step 3 with cyanamide to produce crude creatine monohydrate, then performing crystallization separation, and further performing drying dehydration to produce creatine.

Wherein a chemical reaction for the preparation of creatine takes a sodium salt as an example, specifically:

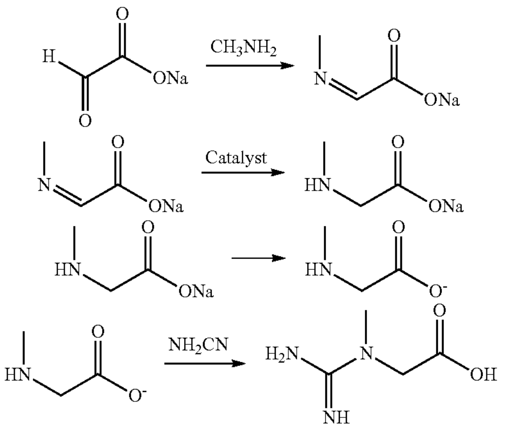

The first three steps of this example were the same as those of the preparation method for creatine monohydrate of Example 3, and mainly the treatment in the step 4 required drying for dehydrating the resulting creatine monohydrate to prepare anhydrous creatine.

Example 5 of the present invention provides a method for the preparation of a creatine salt, including:

step 1, reacting glyoxylic acid or a glyoxylate with an amine to prepare a Schiff base solution;

step 2, adding a catalyst into the resulting Schiff base solution for a hydrogenation reaction;

step 3, adjusting a pH value of a material obtained by the reaction in the step 2 to be between greater than 7 and less than or equal to 11; and step 4, reacting a material obtained in the step 3 with cyanamide to produce creatine, and then adding an alkali to adjust a pH to be greater than 7 to obtain the creatine salt.

Wherein a chemical reaction for the preparation of the creatine salt takes a sodium salt as an example, specifically:

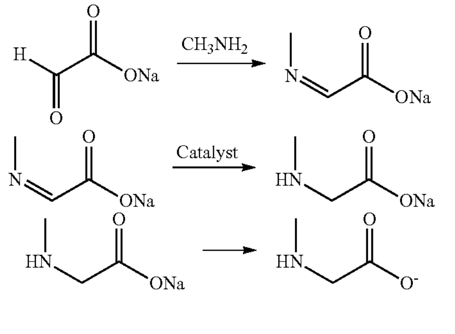

-continued

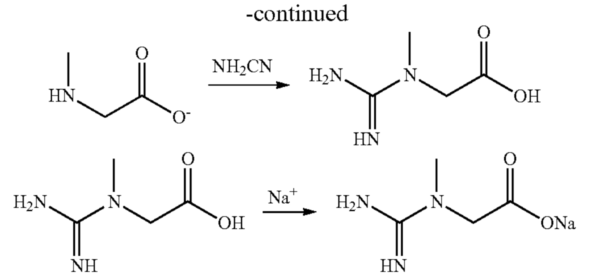

The steps 1-3 of this example were the same as those of the preparation method for creatine monohydrate of Example 3, wherein a pH of a material obtained after the reaction with cyanamide in the step 4 was mainly adjusted to be greater than 7 to obtain the creatine salt, and the pH can be adjusted to be greater than 7 with an alkali (e.g., an inorganic metal hydroxide, inorganic ammonia, an organic amine, alkaline resin or the like). Wherein the alkali was preferably lithium hydroxide, sodium hydroxide, potassium hydroxide, ammonia, methylamine or alkaline resin; wherein the pH value was preferably greater than 9.

Example 6 of the present invention provides a preparation method for a sarcosine derivative and a salt thereof, including:

step 1, reacting glyoxylic acid or a glyoxylate with an amine to prepare a Schiff base solution;

step 2, adding a catalyst into the resulting Schiff base solution for a hydrogenation reaction;

step 3, adjusting a pH value of a material obtained by the reaction in the step 2 to be between 7 or more and 11; and step 4, reacting a material obtained in the step 3 with cyanamide to produce the sarcosine derivative, then adding an alkali, and carrying out a reaction to obtain a salt of the sarcosine derivative corresponding to the sarcosine derivative generated in the step 4.

Wherein an example of a chemical reaction for the preparation of the sarcosine derivative and the salt thereof was specifically as follows:

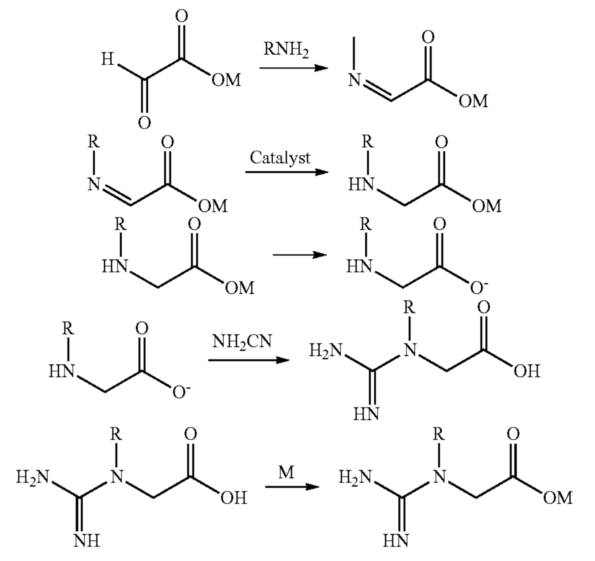

This example was mainly the preparation method for the sarcosine derivative and the salt thereof, wherein M in a general formula for a chemical structure in this example mainly includes: $H^+$, $Li^+$, $Na^+$, $K^+$, $Ca^{2+}$, $Mg^{2+}$, $NH_4^+$, and $RNH_3^+$, preferably $H^+$, $Na^+$ or $K^+$. The R group mainly includes: —H, -Me, -Et, $C_1$-$C_{20}$ alkyl, $C_1$-$C_{20}$ alkenyl, $C_3$-$C_8$ cycloalkyl, or $C_6$-$C_{20}$ aryl, preferably —H or -Me.

The specific preparation examples of the novel preparation method for sarcosine and derivatives thereof of the present invention were further provided below.

Example 7; Example of the Preparation of Sarcosinate by Using Sodium Glyoxylate in a Water-Alcohol System In a three-neck flask of 1 L, 300 g of an aqueous glyoxylic acid solution with a mass percentage concentration of 50% was added, 404 g of a 20% aqueous NaOH solution was added dropwise, and the mixture was stirred for 10 minutes after the dropwise addition, then 252 g of a 40% aqueous methylamine solution was added, and the reaction temperature was controlled to be −10° C., to 40° C., then the mixture was stirred for 30 minutes, then the reaction solution was concentrated and excess methylamine was removed, after concentration of the reaction solution, 1200 mL of methanol and 1.6 g of Pd/C with the palladium content of 10% were added to the concentrated reaction solution, the reaction solution was then transferred into a hydrogenation kettle, and then hydrogen gas was introduced into the hydrogenation kettle to 5 MPa, and a reaction was carried out at room temperature for 8 hours, a material obtained after the reaction was filtered, and then concentrated to remove methanol, and an equimolar amount of alkali (lithium hydroxide, sodium hydroxide, potassium hydroxide, ammonia, methylamine or the like) was added to adjust a pH to be greater than 7 to obtain a corresponding sarcosinate solution.

Example 8: Example of the Preparation of Sarcosinate by Using Glyoxylic Acid in a Water-Alcohol System In a three-neck flask of 1 L, 300 g of an aqueous glyoxylic acid solution with a mass percentage concentration of 50% was added, then 252 g of a 40% aqueous methylamine solution was added, the reaction temperature was controlled to be −10° C., to 40° C., then the mixture was stirred for 30 minutes, then the reaction solution was concentrated, and excess methylamine was removed, after concentration of the reaction solution, 1200 mL of methanol and 1.6 g of 10% Pd/C were added to the reaction solution, the reaction solution was then transferred into a hydrogenation kettle, and then hydrogen gas was introduced into the hydrogenation kettle to 5 MPa, and a reaction was carried out at room temperature for 8 hours, the discharged material was filtered, and concentrated to remove methanol, and an equimolar amount of alkali (lithium hydroxide, sodium hydroxide, potassium hydroxide, ammonia, methylamine or the like) was added to adjust a pH to be greater than 7 to obtain a corresponding sarcosinate solution.

Example 9: Example of the Preparation of Sarcosine by Using Sodium Glyoxylate in a Water-Alcohol System In a three-neck flask of 1 L, 300 g of an aqueous glyoxylic acid solution with a mass percentage concentration of 50% was added, 404 g of a 20% aqueous NaOH solution was added, and the mixture was stirred for 10 minutes after the dropwise addition, then 252 g of a 40% aqueous methylamine solution was added, and the reaction temperature was controlled to be −10° C., to 40° C., then the mixture was stirred for 30 minutes, then the reaction solution was concentrated and excess methylamine was removed, after concentration of the reaction solution, 1200 mL of methanol and 1.6 g of 10% Pd/C were added to the concentrated reaction solution, the reaction solution was then transferred into a hydrogenation kettle, and then hydrogen gas was introduced into the hydrogenation kettle to 5 MPa, and a reaction was carried out at room temperature for 8 hours, then the discharged material was filtered and concentrated to remove methanol, a pH was adjusted to be less than 7 with an acid (sulfuric acid, hydrochloric acid, phosphoric acid, formic acid, acetic acid, acidic resin or the like) to obtain a sarcosine solution, and then the sarcosine solution was concentrated and crystallized to obtain sarcosine.

Example 10: Example of the Preparation of Creatine Monohydrate by Using Sodium Glyoxylate in Water-Alcohol System In a three-neck flask of 1 L, 300 g of an aqueous glyoxylic acid solution with a mass percentage concentration of 50% was added, 404 g of a 20% aqueous NaOH solution was added, and the mixture was stirred for 10 minutes, then 252 g of a 40% aqueous methylamine solution was added, and the reaction temperature was controlled to be −10° C., to 40° C., then the mixture was stirred for 30 minutes, then the reaction solution was concentrated to remove excess methylamine, after concentration of the reaction solution, 800 mL of methanol and 1.6 g of 10% Pd/C were added to the reaction solution, the reaction solution was then transferred into a hydrogenation kettle, and then hydrogen gas was introduced into the hydrogenation kettle to 5 MPa, and a reaction was carried out at 50° C., for 16 hours, then the discharged material was filtered and concentrated to remove methanol, water was added for diluting to 1200 mL, and a pH value of the solution was adjusted to 9.6 with acetic acid (when a pH of the concentrated solution was lower than 9.6, an alkali was used to adjust the pH), and 168 g of a 50% aqueous cyanamide solution was added, the temperature was raised to 70° C., and a reaction was carried out under stirring for 2 hours, the solution was naturally cooled to 30° C., and then separated by centrifugation to obtain 191 g of crude creatine monohydrate, 300 mL of purified water was added to the crude creatine monohydrate, the temperature of the aqueous solution of crude creatine monohydrate was raised to 80° C., and stirring was performed for 30 minutes, then the stirred material was cooled naturally to 30° C., and separated by centrifugation, and then vacuum drying was performed to obtain 141 g of high-purity creatine monohydrate, while controlling the temperature and other parameters so that creatine monohydrate was not dehydrated to prevent creatine monohydrate from becoming creatine due to excessive drying, wherein the purity obtained by high performance liquid chromatography (HPLC) was 99.8%, and no impurities such as creatinine, dicyandiamide and dicyanotriazine were detected.

Example 11: Example of the Preparation of Creatine Monohydrate by Using Glyoxylic Acid in a Water System In a three-neck flask of 1 L, 300 g of an aqueous glyoxylic acid solution with a mass percentage concentration of 50% was added, then 252 g of a 40% aqueous methylamine solution was added, the reaction temperature was controlled at −10° C., to 40° C., the mixture was stirred for 30 minutes, then activated carbon was added for pretreatment, water was added to dilute a filtrate to 1.5 L, 1.6 g of 10% Pd/C was added, the reaction solution was then transferred into a hydrogenation kettle, and then hydrogen gas was introduced into the hydrogenation kettle to 5 Mpa, a reaction was carried out under stirring at 50° C., for 16 hours, then the discharged material was filtered and concentrated, a pH value was adjusted to 9.6 with an alkali, and 168 g of a 50% aqueous cyanamide solution was started to be added, after the dropwise addition, the solution was heated to 70° C., and a reaction was carried out under stirring for 1 hour, the resulting solution was naturally cooled to 20° C., and separated by centrifugation to obtain 191 g of crude creatine monohydrate, 300 mL of purified water was added to the crude creatine monohydrate, and the crude creatine monohydrate solution was heated to 80° C., and stirred for 30 minutes, then naturally cooled to 20° C., separated by centrifugation, and vacuum dried to obtain 136 g of high-purity creatine monohydrate, while controlling the temperature and other parameters so that the creatine monohydrate was not dehydrated to prevent creatine monohydrate from becoming creatine due to excessive drying, wherein the purity of the high-purity creatine monohydrate obtained by high performance liquid chromatography (HPLC) was 99.7%, and no impurities such as creatinine, dicyandiamide and dicyanotriazine were detected in the high-purity creatine monohydrate.

Example 12: Examples of Types and Dosages of Hydrogenation Catalysts in the Preparation of Creatine Monohydrate by Using Sodium Glyoxylate in a Water-Alcohol System In a three-neck flask of 1 L, 300 g of an aqueous glyoxylic acid solution with a mass percent concentration of 50% was added, 404 g of a 20% aqueous NaOH solution was added, the mixture was stirred for 10 minutes, then 252 g of a 40% aqueous methylamine solution was added, the mixture was stirred for 30 minutes, then the reaction solution was concentrated to remove excess methylamine, 800 mL of methanol was added to the reaction solution, a certain amount of catalyst was added, a reaction was carried out, and then the reaction solution was transferred into a hydrogenation kettle, and then hydrogen gas was introduced into the hydrogenation kettle to 5 MPa, and a reaction was carried out at room temperature for 16 hours, and the discharged material was filtered and concentrated to remove methanol, water was added for diluting to 1200 mL, a pH value was adjusted to be 9.3 with acetic acid, and 168 g of a 50% aqueous cyanamide solution was added, after dropwise addition, the temperature was raised to 70° C., and a reaction was carried out under stirring for 2 hours, the resulting reaction solution was naturally cooled to 15° C., and separated by centrifugation to obtain 195 g of crude creatine, 800 mL of purified water was added to the crude product, the temperature was raised to 80° C., and stirring was performed for 30 minutes, then the temperature was lowered to 10° C., separation was performed by centrifugation, and vacuum drying was performed to obtain 140 g of high-purity creatine monohydrate, while controlling the temperature and other parameters so that creatine monohydrate was not dehydrated to prevent creatine monohydrate from becoming creatine due to excessive drying, wherein the purity obtained by high performance liquid chromatography (HPLC) was 99.7%, and no impurities such as creatinine, dicyandiamide and dicyanotriazine were detected. Table 1 shows the experimental results of the hydrogenation reaction under different catalyst dosages.

TABLE 1

Experimental results of hydrogenation reaction under different catalyst types and dosages

| Experiment No. | Hydrogen pressure (Mpa) | Catalyst name | Catalyst dosage (converted to pure) g | Reaction time (h) | Conversion rate (%) |
|---|---|---|---|---|---|
| 1 | 5 | Palladium | 0.2 | 16 | 99.6 |
| 2 | 5 | Palladium | 0.18 | 16 | 99.6 |
| 3 | 5 | Palladium | 0.16 | 16 | 99.4 |
| 4 | 5 | Palladium | 0.14 | 16 | 98.5 |
| 5 | 5 | Palladium | 0.12 | 16 | 96.2 |
| 6 | 5 | Palladium | 0.1 | 16 | 94.8 |
| 7 | 5 | Ni | 0.2 | 16 | 99.6 |
| 8 | 5 | $NaBH_4$ | 0.2 | 16 | 99.6 |
| 9 | 5 | $NaCNBH_3$ | 0.2 | 16 | 99.4 |
| 10 | 5 | $LiBH_4$ | 0.2 | 16 | 99.3 |
| 11 | 5 | Diisobutyl aluminium hydride | 0.2 | 16 | 99.1 |
| 12 | 5 | Iron powder | 0.2 | 16 | 95.1 |
| 13 | 5 | Zinc powder | 0.2 | 16 | 98.5 |
| 14 | 5 | Pt | 0.2 | 16 | 99.6 |
| 15 | 5 | Ru | 0.2 | 16 | 99.3 |
| 16 | 5 | Rh | 0.2 | 16 | 99.7 |

Example 13: Examples of Hydrogenation Reaction Under Different Pressures in the Preparation of Creatine Monohydrate by Using Sodium Glyoxylate in a Water System In a three-neck flask of 1 L, 300 g of an aqueous glyoxylic acid solution with a mass percentage concentration of 50% was added, 282 g of a 32% aqueous NaOH solution was added, the mixture was stirred for 10 minutes, then 252 g of a 40% aqueous methylamine solution was added, and the mixture was stirred for 30 minutes, then 2 g of activated carbon was added into the reaction solution, stirring was performed for 15 minutes, and then filtering was performed, 800 mL of water and 1.6 g of 10% Pd/C were added into the obtained filtrate, and a reaction was carried out, the reaction solution after the reaction was then transferred into a hydrogenation kettle, and then hydrogen gas was introduced into the hydrogenation kettle to 4 MPa, a reaction was carried out for 20 hours at room temperature, the discharged material was filtered, and the obtained filtrate was concentrated to recover methylamine, water was added for diluting to 1200 mL, a pH value was adjusted to 9.8 with an acid (sulfuric acid, hydrochloric acid, phosphoric acid, formic acid, acetic acid, acidic resin or the like), and 280 g of a 30% aqueous cyanamide solution was added, the temperature was raised to 70° C., a reaction was carried out under stirring for 2 hours, the resulting reaction solution was cooled to 20° C., and then separated by centrifugation to obtain 236 g of crude creatine monohydrate, 900 mL of purified water was added into the crude product, the temperature was raised to 80° C., and stirring was performed for 30 minutes, then the temperature was lowered to 10° C., separation was performed by centrifugation, and vacuum drying was performed to obtain 186 g of a high-purity creatine monohydrate finished product, while controlling the temperature and other parameters so that creatine monohydrate was not dehydrated to prevent creatine monohydrate form becoming creatine due to excessive drying, wherein the purity obtained by high performance liquid chromatography (HPLC) was 99.9%, and no impurities such as creatinine, dicyandiamide and dicyanotriazine were detected. Table 2 shows the experimental results of the hydrogenation reaction under different pressures.

TABLE 2

Experimental results of the hydrogenation reaction under different pressures

| Experiment No. | Hydrogen pressure (MPa) | Catalyst dosage (converted to pure) g | Solvent dosage (mL) | Reaction time (h) | Conversion rate (%) |
|---|---|---|---|---|---|
| 1 | 10 | 0.16 | 800 | 16 | 99.9 |
| 2 | 5 | 0.16 | 800 | 16 | 99.8 |
| 3 | 4 | 0.16 | 800 | 16 | 98.6 |
| 4 | 3 | 0.16 | 800 | 16 | 92.6 |
| 5 | 2 | 0.16 | 800 | 16 | 88.5 |
| 6 | 0.5 | 0.16 | 800 | 16 | 30 |
| 7 | 0 | 0.16 | 800 | 16 | 3 |

Example 14: Example of Fixed-Bed Continuous Hydrogenation in the Preparation of Creatine Monohydrate and Anhydrous Creatine by Using Sodium Glyoxylate in a Water System In a three-neck flask of 1 L, 375 g of an aqueous glyoxylic acid solution with a mass percent concentration of 40% was added, 282 g of a 32% aqueous NaOH solution was added, and the mixture was stirred for 10 minutes, then 252 g of a 40% aqueous methylamine solution was added, and the mixture was stirred for 30 minutes, the reaction material was pretreated with activated carbon, filtered and injected into a tubular fixed-bed continuous hydrogenation reactor through a metering pump, wherein a certain amount of Pd/C catalyst has been filled into the fixed bed, and a space velocity of the material was controlled to be 0.1 $h^{-1}$-1.0 $h^{-1}$, the reaction pressure was controlled to be 5 MPa, and the temperature was controlled to be 20-150° C., respectively, after the reaction, a material coming out of the fixed bed was filtered and concentrated, and a pH was adjusted to 9.8, and 280 g of a 30% aqueous cyanamide solution was started to be added, a reaction was carried out under stirring for 2 hours while keeping the temperature at 70° C., and the resulting reaction solution was cooled naturally to 30° C., and separated by centrifugation to obtain 196 g of crude creatine monohydrate, 800 mL of purified water was added into the crude creatine monohydrate, the temperature was raised to 50° C., pulping and stirring were performed for 30 minutes, then natural cooling was performed to 15° C., separation was performed by centrifugation, and vacuum drying was performed at 40° C., for 4 h to obtain 142 g of high-purity creatine monohydrate, wherein the purity obtained by high performance liquid chromatography (HPLC) was 99.9%, and no impurities such as creatinine, dicyandiamide and dicyanotriazine were detected. The creatine monohydrate was further dried to obtain 124 g of a creatine finished product.

Example 15: Example of Fixed-Bed Continuous Hydrogenation in the Preparation of a Creatine Salt by Using Sodium Glyoxylate in a Water System In a three-neck flask of 1 L, 375 g of an aqueous glyoxylic acid solution with a mass percentage concentration of 40% was added, 282 g of a 32% aqueous NaOH solution was added, and the mixture was stirred for 10 minutes, then 252 g of a 40% aqueous methylamine solution was added, and the mixture was stirred for 30 minutes, and then the reaction material was pretreated with activated carbon, filtered and injected into a tubular fixed-bed continuous hydrogenation reactor through a metering pump, wherein a certain amount of Pd/C catalyst has been filled into the fixed bed, and a space velocity of the material was controlled to be 0.1 $h^{-1}$-1.0 $h^{-1}$, the reaction pressure was controlled to be 5 MPa, and the temperature was controlled to be 20-150° C., respectively, after the reaction, a material coming out of the fixed bed was filtered and concentrated, and a pH value was adjusted to 9.8, and 280 g of a 30% aqueous cyanamide solution was started to be added, a reaction was carried out under stirring at 70° C., for 2 hours while keeping the temperature, and the resulting reaction solution was cooled naturally to 30° C., and then an alkali (lithium hydroxide, sodium hydroxide, potassium hydroxide, ammonia or methylamine) with the same molar amount of the cooled product was respectively added into the solution to give a corresponding creatine salt product.

Example 16: Examples of Fixed-Bed Continuous Hydrogenation in the Preparation of Sarcosine Derivatives in a Water System According to the method of the Example of fixed-bed continuous hydrogenation in the preparation of creatine monohydrate and anhydrous creatine by using sodium glyoxylate in the water system, 2 mol of glyoxylic acid or glyoxylate (CHOCOOM) was added into a three-neck flask of 1 L, then 1-6 mol of amine ($RNH_2$) was added, and a reaction was carried out under stirring for a certain time, and the reaction material was pretreated by activated carbon, filtered and injected into a tubular fixed-bed continuous hydrogenation reactor through a metering pump, wherein a certain amount of Pd/C catalyst has been filled into the fixed bed, and a weight hourly space velocity of the material was controlled to be 0.1 $h^{-1}$-1.0 $h^{-1}$, the reaction pressure was controlled to be 5 MPa, and the temperature was controlled to be 20-150° C., respectively

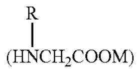

may be obtained from a material coming out of the fixed bed, and then after filtration and concentration, a pH value was adjusted to be 8-11, and cyanamide was started to be added, a reaction was carried out for 2 hours, and then crystallization and solid-liquid separation were performed to obtain a sarcosine derivative ( 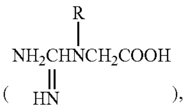 ), and a sarcosine derivative with higher purity can be obtained after extraction. Also an alkali can be added, and a reaction was carried out to generate a corresponding salt of the sarcosine derivative ( 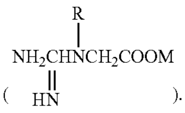 ).

Table 3 is a table showing the experimental products with different substituent groups.

TABLE 3

| Experimental products under different substituent groups | | | |
|---|---|---|---|
| Experiment No. | M | R | product |
| 1 | Na | H | $H_2NCH_2COOH$ |
| | | | $H_2NCH_2COONa$ |
| | | | 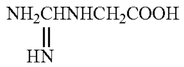 |
| | | | 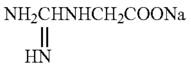 |
| 2 | K | $CH_3$ | 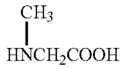 |
| | | | 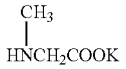 |
| | | | 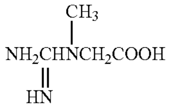 |
| | | | 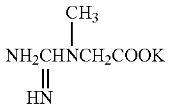 |
| 3 | $NH_3$ | $CH_2CH_3$ | 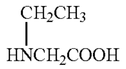 |
| | | | 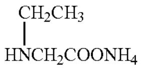 |
| | | | 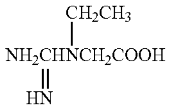 |
| | | | 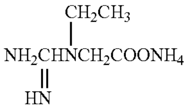 |
| 4 | Na | $C_6H_{12}$ | 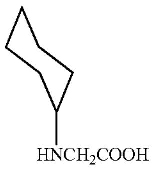 |

TABLE 3-continued

| Experimental products under different substituent groups | | | |
|---|---|---|---|
| Experiment No. | M | R | product |
| | | | 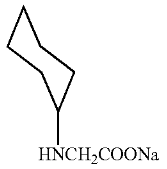 |
| | | | 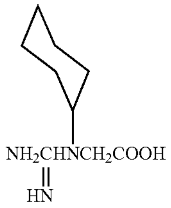 |
| | | | 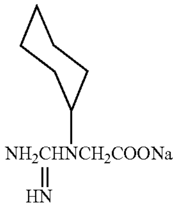 |
| 5 | K | $C_6H_6$ | 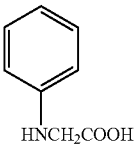 |
| | | | 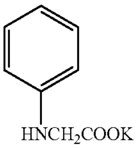 |
| | | | 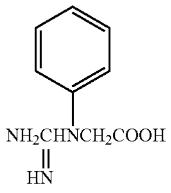 |
| | | | 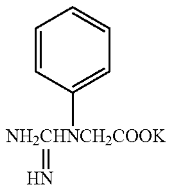 |
| 6 | K | $C_6H_{12}$ | 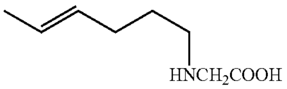 |
| | | | 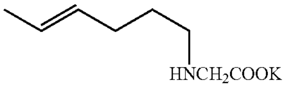 |
| | | | 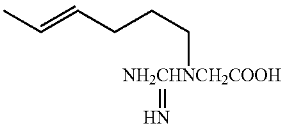 |
| | | | 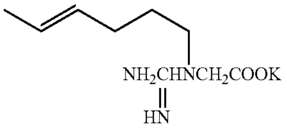 |

The present invention provides the novel preparation method for sarcosine and derivatives thereof, wherein glyoxylic acid or a glyoxylate reacts with an amine to prepare a Schiff base, and the Schiff base is then reduced by a method of catalytic hydrogenation to obtain sarcosine and derivatives thereof. A salt of sarcosine is converted to sarcosine in a free state by means of ion exchange resin, an acid, an alkali and/or electrodialysis. After a sarcosinate solution is adjusted to a desired pH value, creatine monohydrate is prepared by directly reacting an aqueous sarcosinate solution with cyanamide without purification.

In the present invention, non-toxic glyoxylic acid or glyoxylate is used as a starting raw material, the use of toxic raw materials in the prior art is avoided, the impurity system is simple, the reaction condition is mild, the by-products are less, the yield is high, excessive amine in the reaction can be recycled and applied mechanically, the three wastes are less, the process is safe, and the operation is simple and convenient, and thus the method is a green production process suitable for industrial production.

The above are only the preferred embodiments of the present invention, it should be noted that those of ordinary skill in the art can make several modifications and variations without departing from the technical principles of the present invention, and these modifications and variations are also considered to be within the protection scope of the present invention.

What is claimed is:

1. A preparation method for a sarcosinate, characterized by comprising:

step 1, reacting a solution of glyoxylic acid or a glyoxylate with a methylamine solution to prepare a Schiff base solution;

step 2, subjecting the prepared Schiff base solution to a hydrogenation reaction under the condition of a catalyst and under a pressure of 5 MPa to 10 MPa; and step 3, adjusting a pH value of a solution obtained after the hydrogenation reaction to be alkaline to obtain the sarcosinate.

2. The preparation method of claim 1, characterized in that, a general formula for a chemical structure of glyoxylic acid is:

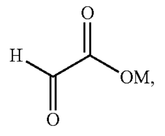

wherein M is $H^+$;

a general formula for a chemical structure of the glyoxylate is:

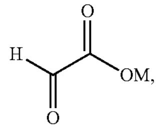

wherein Mis $NH_4^+$, $RNH_3^+$, $Li^+$, $Na^+$, $K^+$, $Ca^{2+}$ or $Mg^{2+}$; and a general formula for a chemical structure of a Schiff base is:

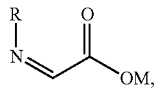

wherein the R group is Me.

3. The preparation method of claim 1, characterized in that, in the step 2, the hydrogenation reaction adopts an intermittent catalytic hydrogenation reaction, a fixed-bed continuous catalytic hydrogenation reaction or a fixed-bed semi-continuous catalytic hydrogenation reaction; and a solvent for the hydrogenation reaction is H2O/R'OH, wherein R' is C1-C6 alkyl;

wherein the intermittent hydrogenation reaction is carried out for 8-16 hours;

wherein the amount of a catalyst used in the intermittent hydrogenation reaction is 0.01 wt %-2 wt %;

wherein a weight hourly space velocity of the fixed-bed continuous catalytic hydrogenation is 0.2 $h^{-1}$-0.5 $h^{-1}$.

4. The preparation method of claim 1, characterized in that, in the step 1, the amount of the methylamine used in the methylamine solution is 1-6 equivalents;

the methylamine solution is an aqueous or alcoholic solution of the methylamine, the aqueous or alcoholic solution of the methylamine having a mass percent concentration of 30% to 40%.

5. The preparation method of claim 1, characterized in that, the solution of glyoxylic acid or glyoxylate is reacted with the methylamine solution at a temperature of −10° C. to 40° C.

6. The preparation method of claim 1, characterized in that, in the step 2, a solvent system for the hydrogenation reaction is an alcohol plus water system or a water system;

wherein a volume ratio of the water to the alcohol is 1:0-1:2.

7. The preparation method of claim 1, characterized in that, in the step 2, the catalyst is one or more of Pd, Ni, Pt, Ru, Rh, NaBH4, NaCNBH3, LiBH4, diisobutyl aluminium hydride, iron powder and zinc powder;

wherein a carrier of the catalyst is alumina, zeolite, activated carbon, SiO2, ceramic balls, sea sand, graphite, inorganic glass, organic glass, optical fiber, glass fiber, natural clay, foamed plastic, resin, wood chips or expanded perlite.

8. The preparation method of claim 1, characterized in that, in the step 2, the hydrogenation reaction is carried out at a temperature of 30-100° C.

9. The preparation method of claim 1, characterized in that, in the step 3, the pH value of the solution is adjusted to a desired alkaline value after the solution is treated by an acid, an alkali, electrodialysis or ion exchange resin depending on the pH value of the solution.

10. The preparation method of claim 9, characterized in that, in the step 3, the acid is an inorganic acid or an organic acid; the alkali is an inorganic metal hydroxide, inorganic ammonia or an organic amine; and the ion exchange resin is acidic ion exchange resin or alkaline ion exchange resin.

11. A preparation method for creatine, characterized in that, a sarcosinate solution is prepared by using the preparation method of any one of claims 1-10, and the method further comprises:

step 4, reacting the sarcosinate solution with cyanamide to prepare the creatine.

12. The preparation method of claim 11, characterized in that, the creatine is anhydrous creatine, creatine monohydrate or a creatine salt.

13. The preparation method of claim 12, characterized in that, after the sarcosinate solution is reacted with cyanamide, crystallization separation is performed to prepare creatine monohydrate.

14. The preparation method of claim 12, characterized in that, after the sarcosinate solution is reacted with cyanamide, crystallization separation and drying dehydration are performed to prepare creatine.

15. The preparation method of claim 11, characterized in that, the pH value of the solution obtained after the hydrogenation reaction is adjusted to be greater than 7 and less than or equal to 11.

16. The preparation method of claim 12, characterized in that, after cyanamide is added into the sarcosinate solution for a reaction, an alkali is added, and a pH value is adjusted to be greater than 7 to obtain the creatine salt.

17. The preparation method of claim 11, characterized in that, after cyanamide is added into the sarcosinate solution for a reaction, an alkali is added, and a pH value is adjusted to be greater than 7 to obtain a creatine salt.

18. A preparation method for sarcosine, characterized in that, steps 1 and 2 of the preparation method of any one of claims 1-9 are carried out, and then, in step 3, the pH value of the solution obtained after the hydrogenation reaction is adjusted to be acidic to obtain the sarcosine.

19. The preparation method for sarcosine of claim 18, characterized in that, in the step 3, the pH value of the solution is adjusted to be acidic after the reaction solution obtained after the hydrogenation is treated by an acid, electrodialysis or acidic ion exchange resin.

20. The preparation method for sarcosine of claim 19, characterized in that, in the step 3, the acid is an inorganic acid or an organic acid.

* * * * *